United States Patent [19]

Steer et al.

[11] Patent Number: 4,986,824
[45] Date of Patent: Jan. 22, 1991

[54] OSTOMY COUPLING INCLUDING GAS FILTER CARTRIDGE

[75] Inventors: Peter L. Steer, Sussex; Neil P. Wiltshire; David J. Auld, both of Surrey, all of England

[73] Assignee: E. R. Squibb & Sons, Inc., Princeton, N.J.

[21] Appl. No.: 449,033

[22] Filed: Dec. 11, 1989

[30] Foreign Application Priority Data

Dec. 14, 1988 [GB] United Kingdom ................ 8829134

[51] Int. Cl.⁵ ................................................ A61F 5/44
[52] U.S. Cl. ..................................... 604/333; 604/338
[58] Field of Search .............. 604/333, 334, 332, 341, 604/342, 338, 339; 55/385.4, 359

[56] References Cited

U.S. PATENT DOCUMENTS

| 4,232,672 | 11/1980 | Steer et al. | 128/283 |
| 4,268,286 | 5/1981 | Steer et al. | 55/278 |
| 4,451,258 | 5/1984 | Jensen | 604/333 |
| 4,460,363 | 7/1984 | Steer et al. | 604/336 |
| 4,834,732 | 5/1989 | Steer et al. | 604/342 |
| 4,940,461 | 7/1990 | Steer | 604/333 |

FOREIGN PATENT DOCUMENTS

| 191646 | 6/1986 | European Pat. Off. . |
| 87/01274 | 4/1987 | PCT Int'l Appl. . |
| 1571657 | 7/1980 | United Kingdom . |
| 1595906 | 4/1981 | United Kingdom . |
| 2121902 | 10/1984 | United Kingdom . |
| 2177926 | 6/1987 | United Kingdom . |

Primary Examiner—Randall L. Green
Assistant Examiner—Gina M. Gualtieri
Attorney, Agent, or Firm—Stephen B. Davis

[57] ABSTRACT

A bagside coupling for an ostomy bag is intended to cooperate with a filter cartridge. Inserting the filter cartridge in a suitable recess results in establishing connection between the interior of the bag and the exterior. Escaping gases are constrained to pass through filter material in the filter cartridge.

6 Claims, 2 Drawing Sheets

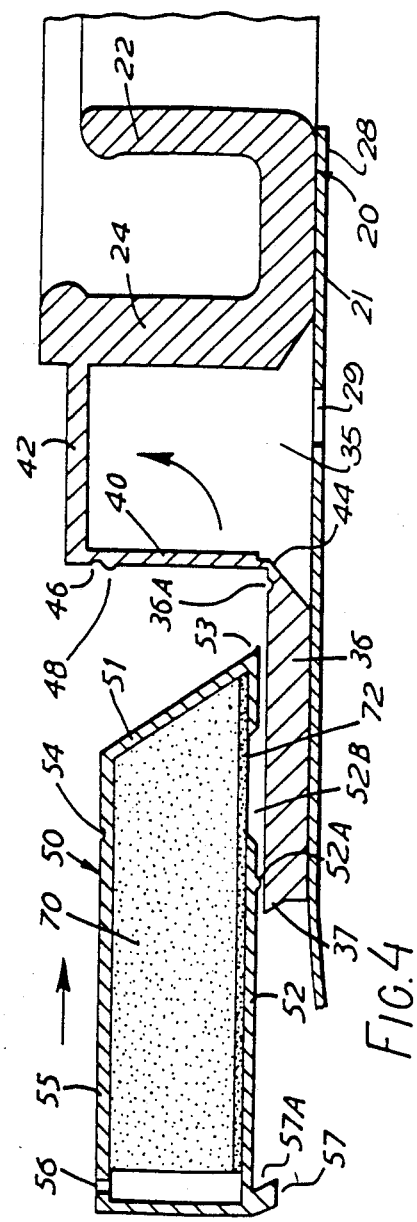
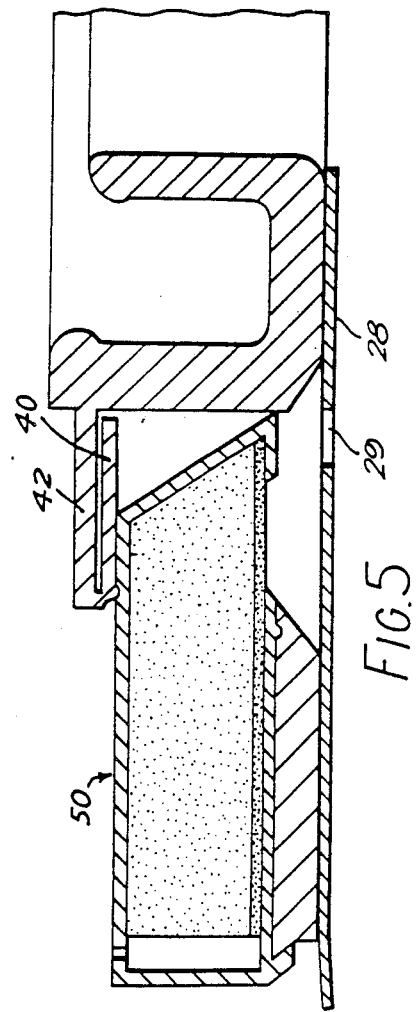

OSTOMY COUPLING INCLUDING GAS FILTER CARTRIDGE

BACKGROUND OF THE INVENTION

This invention relates to an ostomy coupling which may optionally be used with a gas vent and filtering means. It also relates to a filter cartridge.

The prior art is replete with suggestions intended to permit flatus gases to be vented from an ostomy bag. Many such arrangements included means for deodorizing these gases by the use of filters of various kinds. One successful ostomy bag and coupling arrangement is disclosed in British Pat. No. 1 571 657 of Kingsdown Medical Consultants Limited. As illustrated in FIG. 5 of that patent, a passageway radially through a coupling element allows escape of gas. In British Pat. No. 2 121 902, a bagside coupling element includes structure providing a recess which may house filter material. The bag wall is punctured to allow gas to escape from the bag into the recess, from which it escapes to atmosphere through a slit in the housing wall after having passed through a filter pad. An ostomy coupling element which is integral with a filter housing that can be closed by a snap-in cover is disclosed in British patent application Ser. No. 2 177 926A. A similar concept employing a separate filter housing is disclosed in U.K. patent application Ser. No. 2 202 147.

These and other attempts at achieving satisfactory deodorization of flatus gases have met certain needs but have increased the complexity of manufacture of ostomy bags, and the inventory which manufacturers need to carry, because of the need to manufacture two kinds of bag, namely those with filters and those without. Moreover, a patient having having purchased non-filter bags cannot change over to using a filter type without scrapping his stock of bags and purchasing new ones.

It would be desirable if there existed a bagside coupling for an ostomy bag which was satisfactory on a non-filter type bag but which could still be used, without modification, if the wearer wished to employe a filter.

It is an aim of the invention to meet this need.

SUMMARY OF THE INVENTION

In accordance with one aspect of the invention, there is provided a bagside coupling for an ostomy bag comprising a coupling element designed for cooperation with a bodyside coupling element and having a stomal orifice, the coupling element having, adjacent to the stomal orifice, structure defining a recess and having a wall with a line of weakening therein, the wall separating the stomal orifice space from the space within the recess.

Such a coupling element can be used as a conventional coupling element attached to a bag when no provision for gas venting and filtering is desired.

It can alternatively be used, in conjunction with a special filter cartridge which will be described later, when gas venting and filtering is desired. In this case, the cartridge is designed and dimensioned so that it can be pushed into the recess whereupon a blade like edge of the cartridge penetrates and breaks the line of weakening. As a result of this, gas within the bag can flow into the cartridge and through the filtering/deodorizing medium therein. The gas leaves the cartridge to pass into the ambient atmosphere through one or more gas exit holes in the cartridge wall.

According to another aspect of the invention, there is provided a filter cartridge comprising a box-like casing containing a filter medium, the casing having entry and exit holes for gas, and walls at one end which are formed to provide a blade-like edge, the gas entry hole being adjacent to the said one end.

Advantageously, the filter cartridge is made of a slightly resilient plastics material, its blade-like edge may be serrated, and its walls may have ribs and grooves on their external surfaces to cooperate with counterpart grooves and ribs on a cartridge-holder. Also advantageously, a layer of microporous water repellent material may be placed to protect the filter medium in the region of the gas entry hole.

Preferably the cartridge-receiving recess in the coupling element is rectangular as seen in a lateral cross-section and preferably the recess is substantially at the "10 o'clock" position in relation to a bagside coupling element having a substantially circular stomal orifice. It is in any event desirable for the recess to be located on the upper half of the coupling element. In this paragraph, the words upper and lower are used as applying to the bag and the coupling when they are in the normal position as worn by a patient standing upright.

The recess need not be rectangular. It could be circular or oval as seen in lateral cross-section in which case the filter cartridge would be likewise circular or oval. The cartridge could contain a pad of open-cell polyurethane foam loaded with activated carbon, or it could contain carbon particles, or it could contain other filtering and deodorizing media.

Preferably there are provided interengaging means whereby the cartridge is securely held in the recess once inserted, so that it cannot be dislodged by the normal movements of the wearer.

BRIEF DESCRIPTION OF THE DRAWINGS

The invention will be better understood from the following non-limiting description of an example thereof given with reference to the accompanying drawings in which:

FIGS. 4 and 5 are partial cross-sectional views on the line A—A of FIG. 1, showing the bagside coupling element and the filter cartridge just prior to insertion of the latter and when inserted respectively.

DETAILED DESCRIPTION OF THE DRAWINGS

Figure 1:
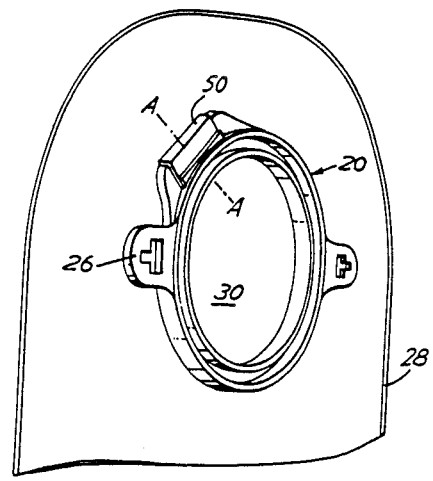
FIG. 1 is a perspective view of one example of bagside coupling according to the invention attached to an ostomy bag, with filter cartridge inserted.

Referring to the drawings, the illustrated bagside coupling element 20 according to the invention includes radially inner and outer walls 22, 24 defining a channel section for reception of a complementary bodyside coupling. For a description in greater detail of a coupling of this kind the reader is referred to British Pat. No. 1,571,657. The invention may, however, be applied to other types of coupling. The element 20 has ears 26, as is conventional, for belt or harness attachment, which is however optional. The coupling element 20 is shown attached to an ostomy bag 28 and the channel section portion encircles a stomal orifice 30. Such coupling elements are customarily molded from synthetic plastics materials.

Figure 2:
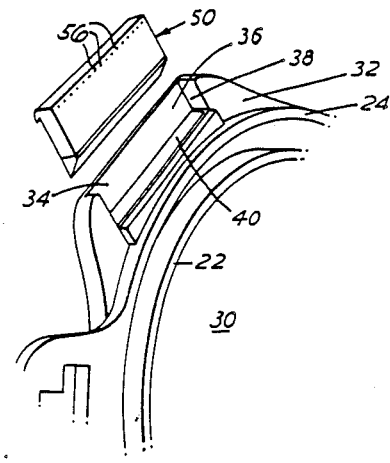
FIG. 2 is a perspective view on an enlarged scale, showing the filter cartridge just prior to insertion.
Figure 3:
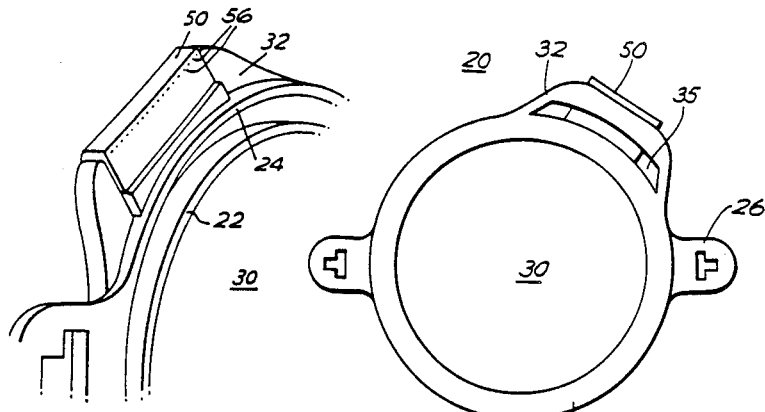
FIG. 3 is a view similar to FIG. 2 but showing the cartridge in place.
Figure 6:
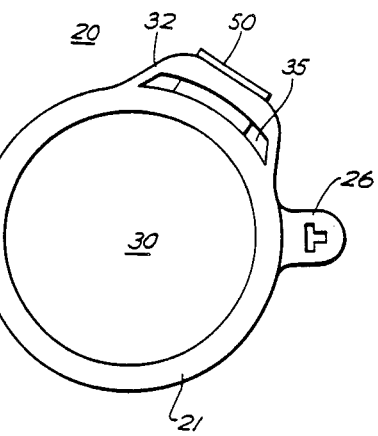
FIG. 6 is a bottom view of the bagside coupling element of FIGS. 1-5 with the cartridge in place.

The coupling element 20 has a structure 32 coupled to and extending away from the channel section (which is preferably molded in one operation with the rest of the element 20) defining a recess 34 (FIG. 2). The recess is open-topped and substantially rectangular in lateral cross-section. It is defined by a rear wall 36, side walls 38, and a base wall 40. The bag is attached to the underside 21 of coupling element 20 as well as the underside surface of rear wall 36. A gap 35 exists between the wall 36 and wall 24 and this is in registry with a hole or slit 29 in the bag wall attached to the coupling element to allow gas to escape from the bag.

The filter cartridge 50 has the approximate shape of a thin rectangular box and contains a filtering medium. As seen best in FIGS. 4 and 5, its lower wall 51 and its rear wall 52 has a rib or pip 52A projecting therefrom which extends substantially the whole way across the rear wall 52. A groove 54 extends across the front wall 55, the latter having a gas exit hole or holes 56 at its upper region. An undercut projection 57 is located at the upper edge of the rear wall 52 for a reason which will appear later.

The base wall 40 of the recess is connected to the wall 24 by a wall 42, and has a line of weakening 44 formed by a thinned section extending across its full width. It also has a groove 46 which acts as a weakening to a lesser extent. The groove 46 forms a fold line when the filter cartridge is inserted as will be understood by comparing FIGS. 4 and 5. The wall 40 also has a rib 48 on its other surface whose function is to engage in the groove 54 as seen in FIG. 5 when the cartridge 50 is in its inserted position. Likewise, the rib 52A engages in a groove 36a provided in wall 36 once the cartridge is fully inserted. The engagements between ribs 48, 52a and grooves 5A, 36A serve to hold the filter cartridge securely in its inserted condition. However, the grooves are not made so deep, nor the ribs so high, that the engagement is too secure for the cartridge to be manually removed. The upper margin of the wall 36 is shaped to provide an acute-angled edge 37 which engages in the re-entrant 57A formed by the projection 57 when the cartridge is fully inserted. This tends to prevent flexing of the cartridge under stress and hence tends to prevent any separation between the wall 52 of the cartridge and the wall 36 of the coupling element 20. This is a useful feature as it is important to preclude gas bypassing of the filter. The cartridge wall 52 has a substantially rectangular hole 52B for inflow of gas to be deodorized. In the inserted position of the cartridge this hole 52B is located substantially in registry with the gap 35 between the walls 36 and 24 of the coupling element and hence gas can pass directly and unobstructedly from the interior of the bag 28 through hole or slit 29 into the filter medium 70 within the cartridge and out the gas exit holes 56. As an optional refinement, a layer 72 of a microporous water repellent material (such as those known as "MICROPORE" or "GORETEX") may be placed over or secured to the rear surface of the filter medium 70. This is a useful expedient, to protect and keep dry the filter medium, when it is expected that the ostomy bag will be sold to those who have a high liquid content in their discharged wastes.

In use, insertion of the filter cartridge 50 breaks the line of weakening 44 and bends down the wall 40. The ribs and grooves 48, 52A, 36A, 54 act as a locking means and engage as does the "latch" 37, 57A. The filter cartridge can be removed manually by simply withdrawing it and a fresh one can readily be inserted. Alternatively, the coupling element as disclosed, prior to rupture along the line 44, is perfectly suitable for use on a non-filter type bag, and hence only one (readily molded) type need be manufactured for both purposes.

Once inserted, the cartridge 50 fits snugly in the recess 34, and the chance of gas bypass is remote.

What is claimed is:

1. A bagside coupling attached to an ostomy bag comprising a coupling element designed for cooperation with a bodyside coupling element and having a portion which surrounds a stomal orifice, the coupling element having structure coupled to and extending away from said portion, said structure defining a recess and having a wall with a line of weakening therein, the wall separating a space adjacent said portion from the space defined by the recess; said space adjacent said portion being in communication with the interior of said bag through an opening therein; and a filter cartridge comprising a box-like casing containing a filter/deodorizing medium, the casing having entry and exit holes for gas, and walls at one end which are formed to provide a blade-like edge, the gas entry hole being adjacent to said one end, said filter cartridge designed and dimensioned so that it can be pushed into the recess whereupon said blade like edge of the cartridge penetrates and breaks the line of weakening, so that gas within the bag flows into the cartridge and through the filter medium therein, and gas leaves the cartridge to pass into the ambient atmosphere through said gas exit holes.

2. A coupling element according to claim 1 which includes locking means wherein the cartridge is securely but removably held in the recess once inserted, so that it cannot be dislodged by the normal movements of the wearer.

3. A bagside coupling according to claim 2 wherein said filter cartridge is made of a resilient plastics material having walls, said locking means comprising ribs and grooves on external surfaces of said filter cartridge walls which cooperate with counterpart grooves and ribs on said structure to lock said cartridge to said coupling.

4. The bagside coupling of claim 3 wherein said locking means comprises a groove carried by said casing and a mating rib and said wall with a line of weaking, which groove and mating rib snap together when said cartridge is pushed into said recess.

5. A cartridge according to claim 1 in which a layer of microporous water repellent material is placed to protect the filter medium in the region of the gas entry hole.

6. A coupling element according to claim 1 in which the cartridge receiving recess is rectangular and said portion of said coupling has a substantially circular stomal orifice.

* * * * *